United States Patent [19]

Barda

[11] 4,223,169

[45] Sep. 16, 1980

[54] PROCESS FOR POLYBROMINATING BISPHENOXYALKANES

[75] Inventor: Henry J. Barda, Bedford Heights, Ohio

[73] Assignee: Ferro Corporation, Cleveland, Ohio

[21] Appl. No.: 874,765

[22] Filed: Feb. 3, 1978

Related U.S. Application Data

[63] Continuation-in-part of Ser. No. 664,628, Mar. 8, 1976, abandoned.

[51] Int. Cl.³ .............................................. C07C 41/22
[52] U.S. Cl. ................................................... 568/645
[58] Field of Search ...................... 260/613 R; 568/645

[56] References Cited

U.S. PATENT DOCUMENTS

| | | | |
|---|---|---|---|
| 1,306,472 | 6/1919 | Dow | 260/662 R |
| 2,022,634 | 11/1935 | Britton et al. | 568/639 |
| 2,591,498 | 4/1952 | Betts, Jr. et al. | 252/386 |
| 2,607,802 | 8/1952 | Britton et al. | 260/612 R X |
| 2,658,086 | 11/1953 | Ruh et al. | 260/653.8 |
| 3,012,035 | 12/1961 | Knowles et al. | 544/303 |
| 3,285,965 | 11/1966 | Jenkner | 260/612 R |
| 3,449,443 | 6/1969 | Dietzler et al. | 568/746 |
| 3,845,146 | 10/1974 | Moore et al. | 260/612 R X |
| 3,965,197 | 6/1976 | Stepniczka | 260/607 R |
| 4,016,137 | 4/1977 | Anderson et al. | 260/45.75 R |
| 4,016,139 | 4/1977 | Anderson et al. | 260/45.75 R |
| 4,032,507 | 6/1977 | Anderson et al. | 260/45.75 R |
| 4,032,508 | 6/1977 | Anderson et al. | 260/45.75 R |

FOREIGN PATENT DOCUMENTS 874062 8/1961 United Kingdom .
934970 8/1963 United Kingdom .

OTHER PUBLICATIONS

Raiford et al., JACS., vol. 51 (1929) 1776–1778.
Brewster, Organic Chemistry (1953) 494–496, 515.
Burwell, Chemical Reviews, vol. 54 (1954) 628, 630, 654.
Fieser and Fieser, Advanced Org. Chem., (1961) 630–631, 773–775, 780–781 & 787.
Hashem, J. Appl. Chem. Biotechnol. (1974), vol. 24, 59–61.

*Primary Examiner*—Bernard Helfin
*Attorney, Agent, or Firm*—Irons and Sears

[57] ABSTRACT

A process is disclosed for the essentially complete bromination of bisphenoxyethane and bisphenoxypropane, and their substitution products, with minimal cleavage of the phenoxy-to-alkylene linkages, characterized by reacting the bisphenoxyalkane reactant with a stoichiometric excess of bromine chloride in the presence of a Lewis acid catalyst and a chemically inert organic solvent adapted to dissolve all of such reactants and the catalyst. Optionally, the bisphenoxyalkane reactant and the resulting product of the process may have alkyl and chlorine substituents in either or both phenyl groups.

34 Claims, No Drawings

PROCESS FOR POLYBROMINATING BISPHENOXYALKANES

RELATED APPLICATION

This application is a continuation-in-part of my earlier-filed copending application, Ser. No. 664,628, filed Mar. 8, 1976, now abandoned.

BACKGROUND OF THE INVENTION

Highly brominated aryl alkyl ethers have utility as fire retardants for organic, polymeric resinous materials. See, for example, U.S. Pat. Nos. 3,658,634; 3,717,609; 3,808,171; 4,016,137; 4,016,139; 4,032,507; and 4,032,508; and Japanese Pat. No. 14,500 (72). In common with other highly halogenated molecules, such as, for example, many of those disclosed in U.S. Pat. Nos. 3,403,306 and 3,418,263, many of the highly brominated aryl alkyl ethers, when compounded in plastics and exposed to sunlight, are subject to discoloration. With many, a gradual yellowing occurs that is undesirable and that is frequently masked by the use of dark brown pigments or even paint. There is a need for light stable fire retardant additives for plastics. As a general rule, the more bromination that can be achieved in the aryl group, the more effective the compound is as a fire retardant. Heretofore it has been difficult to brominate to as much as three bromine atoms per phenyl group in bisphenoxyalkanes, and most difficult if not impossible completely to brominate the phenyl group in bis-phenoxyalkanes, without cleaving one or both of the phenoxy-to-alkylene linkages.

One way of making the highly brominated bisphenoxyalkane compounds, that is disclosed in U.S. Pat. No. 4,016,137, for example, involves reacting a brominated phenol with an alkylene halide. This is itself an acceptable synthesis step, but there is a great practical difficulty in producing a brominated phenol that contains four or five bromines per molecule. To date the production of such highly brominated phenols has been so difficult as to prevent their use for the further step of producing the brominated bisphenoxyalkanes on a practical, commercial basis.

To produce highly brominated aromatic compounds, especially fully brominated compounds, rigorous reaction conditions have been considered necessary, i.e., high temperatures, and large amounts of active catalyst. Under these conditions, if elemental bromine is used as the brominating agent, hydrogen bromide is produced as a by-product, and this degrades the product formed. In addition, it is wasteful of bromine. Similarly, under such conditions, the use of Lewis acid catalysts for the bromination also resulted in degradation of the product. When the aromatic compound being brominated is a bisphenoxyalkane, cleavage of the phenoxy-to-alkylene linkage occurs. Hydrogen bromide causes the formation of phenols, R. L. Burwell, Chem. Rev. 54, at 630 (1954), and Lewis acid catalysts promote the formation of phenol salts, idem. at 654. Diphenyl ether, however, is not cleaved by strong acids, idem. at 628.

Thus brominated anisoles when heated with hydrogen bromide in acetic acid for two hours on a steam bath decompose to an extent of 21–85%. D. M. Birosel, J. Am. Chem. Soc., 53, 1408 (1931). When anisole is heated for two hours at 100° C. with aluminum chloride, methyl chloride evolves and leaves behind $Cl_2AlOC_6H_5$. G. Baddeley, J. Chem. Soc. 1944, 330. When the bromination of anisole is catalyzed by aluminum chloride, Bonneaud, Bull. Soc. Chim., Fr. (4)7, 776 (1910), or iodine, A. I. Hashem, J. Appl. Chem. Biotechnol, 24, 59 (1974), only pentabromophenol is recovered. Thus anisoles cannot survive drastic bromination conditions. Under mild conditions a maximum of three bromine atoms can be introduced per aromatic ring. The practicality of introducing even three bromine atoms per aromatic ring under non-degrading reported conditions is questionable.

The bromination of anisole with one equivalent of bromine is chloroform, at room temperature, is reported to give an 80% yield of monobromoanisole. Grignard, Bellet and Courtot, Ann. Chim. 4, 28 (1915). The preparation of dibromoanisole from anisole, and of tribromoanisole from dibromoanisole, in carbon tetrachloride, is also reported. Kohn and Sussman, Monatsh. Chem. 46, 575 (1925). "Several days" reaction time is reported for the preparation of several tribromophenyl alkyl ethers. Yields are not reported. Baiford and Birosel, J. Am. Chem. Soc., 51, 1776 (1929). The bromination of anisole with three equivalents of bromine yields 1.5% tribromoanisole. Similarly, the bromination of monobromoanisole with two equivalents of bromine in chloroform is reported to give only small quantities of tribromoanisole, and tribromoanisole is reported not to brominate further. D. M. Birosel, Univ. Phillipines Natural Applied Sci. Bull. 1, 145 (1931).

The monobromination of anisole with a solution containing chlorine and bromine is one of the examples listed in U.S. Pat. No. 2,607,802 (1951).

1,2-Bis(4-bromophenoxy)ethane has been prepared in 50–70% yield by reaction of bromine in acetic acid. A. C. Cope, J. Am. Chem. Soc., 57, 572 (1935). A tetrabrominated derivative of 1,2-diphenoxyethane is reported by bromination in chloroform. Lippman, C. R., Acad. Sci., 68, 1269 (1869).

Bis(tribromophenoxy)-ethane and bis(tetrabromophenoxy)ethane have been prepared from brominated phenols and ethylene dibromide, by utilizing the brominated phenol as a reactant. M. Kohn and A. Fink, Monatsh. Chem., 44, 194 (1924). Dow has been granted a patent for the polybromination, with bromine chloride, of aromatic compounds other than aryl alkyl ethers, in a closed system. U.S. Pat. No. 3,845,146 (1974).

Accordingly, a dilemma faces one seeking the production of highly brominated aryl alkyl ethers. If conditions conducive to substantial bromination are used, such as strong Lewis acids and relatively high temperatures, then degradation and cleavage of the phenoxy-to-alkylene linkage results. If, to avoid this, milder conditions are used, such as no catalyst or a weak Lewis acid catalyst and relatively low temperatures, then an unsatisfactory, low level of bromination results.

It would, therefore, advance the art to be able to produce highly brominated bisphenoxyalkanes, especially at relatively high yields, in a manner which does not degrade the product nor cleave the phenoxy-to-alkylene linkage.

SUMMARY OF THE INVENTION

According to the present invention, a bisphenoxyalkane having two or three carbon atoms in the alkane moiety is polybrominated with a stoichiometric excess of bromine chloride in the presence of a Lewis acid catalyst and a chemically inert organic solvent adapted to dissolve all of the reactants. A fully brominated product is formed having the formula:

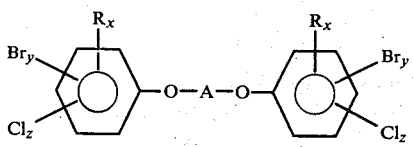

in which A is alkylene of two or three carbon atoms; R is alkyl up to and including four carbon atoms; x is 0, 1 or 2; y is 3, 4 or 5; and z is 0, 1 or 2. It is understood that each of R, x, y and z may be the same or different on the phenyl groups.

Preferably the Lewis acid catalyst is a metal halide Lewis acid catalyst capable of effecting a Friedel-Crafts reaction, and the chemically inert organic solvent is a chlorinated aliphatic hydrocarbon. In general, solvents having no carbon to carbon unsaturation is preferred. The process may be carried out at a temperature within the range of about minus 10° C. to about 150° C. and at a pressure of about atmospheric to about 200 pounds per square inch gage (psig). Yields of at least 77% of the product are possible, and yields of 90% and higher are common.

The process of the present invention includes the use of both relatively strong and relatively weak Lewis acid catalysts. When relatively strong Lewis acid catalysts are used, after formation of the product and prior to recovering it, water is added to the solvent to destroy the catalyst.

Products produced in accordance with the invention can be used as additives to make fire retarded plastic compositions. The bis(pentabromophenoxy)ethane reaction product is particularly useful for this purpose. For effective fire retardance, the plastic material is blended with the reaction product and a co-additive such as antimony trioxide. The amounts to be used will be apparent to those skilled in the art, based upon the bromine content of the reaction product, the particular host plastic, and the co-additive selected. Especially good results are obtained with ABS and polystyrene resins, with polyolefins, and with polyesters, in all of which the outstanding light stability of the essentially fully brominated reaction products of the invention is an important property.

The preferred product of the process is bis(pentabromophenoxy)ethane. The 1,2-bis(pentabromophenoxy)ethane product produced by the process of the present invention is a filler-type fire retardant additive for polymeric compositions. It exhibits a high degree of thermal and ultraviolet light stability as well as low volatility, which properties are beneficial in many plastics applications.

Analytically pure 1,2-bis(pentabromophenoxy)ethane contains 79.6% bromine by weight. It has a melting point of 323°–324° C. as determined visually on a Mel-temp apparatus. The melting point as determined by differential scanning colorimetry (DSC) is 318°–326° C. The volatility as determined by thermogravimetric analysis (TGA) is as follows:

$T_0$: 320° C.
$T_1$: 330° C.
$T_5$: 342° C.
$T_{10}$: 347° C.
$T_{25}$: 357° C.
$T_{50}$: 366° C.

DESCRIPTION OF THE PROCESS

Considering in greater detail the components and conditions of the present process, only those bisphenoxyalkanes or substituted bisphenoxyalkanes having two or three carbon atoms in the alkane moiety are useful as substrates for high yield production of fully brominated products. When there are more than three carbon atoms in the alkylene bridge, cleavage and/or degradation occur, with serious effects upon the yield of fully brominated products. Moreover, such ethers with only one carbon atom in the alkylene bridge are believed to be subject to cleavage at the phenoxy-to-alkylene linkage.

Bisphenoxyalkanes charged to the process may have alkyl and chloro substituents as shown, for example, by Formula (1) of the preceding section. Similarly, some bromination may or may not be present in the material charged, although of course not to the extent capable of being achieved by the present process.

To make the preferred product, bis(pentabromophenoxy)ethane, the starting material may be 1,2-diphenoxyethane, or a substituted or partially brominated derivative thereof. The preferred starting material is commercially available or laboratory-prepared 1,2-diphenoxyethane. It is generally 97% pure or better. As used in the examples described in this application, its color has varied from white to reddish tan. Whether obtained commercially or prepared in the laboratory, it often has a small amount, much less than 1% by weight, of a material that is insoluble in 1,1,2,2-tetrachloroethane (hereafter referred to as tetrachloroethane or as ATC, or acetylene tetrachloride).

The brominating agent is bromide chloride. Bromine chloride is an equilibrium mixture of bromine, chlorine, and bromine chloride. The bromine chloride is used as an anhydrous system. The bromination proceeds to the virtual but not complete exclusion of chlorination. Most or all of the chlorine present in the brominating agent is converted to HCl which escapes as a gas. Use of bromine chloride as the brominating agent is thought to be highly contributory to avoiding the phenoxy-to-allkylene cleavage. Bromine chloride enables the process to proceed under milder conditions, such as a lower temperature, than otherwise would be the case when bromine alone is used. Indeed, the present process proceeds at room temperature. Bromine chloride also enables the use of less strong Lewis acid catalysts which further contributes to avoiding the cleavage of phenoxy-to-alkylene linkage.

The manner of preparing bromine chloride is known in the art. Conveniently, bromine and chlorine are mixed in a closed container and the bromine chloride formed is withdrawn from the liquid phase. Bromine and chlorine may be used in a molecular ratio of from about 0.7:1 to about 1.3:1 and preferably from about 0.9:1 to 1.1:1, respectively. If the ratio of bromine to chlorine substantially exceeds that indicated, the process is operational but HBr is formed as a by-product. HBr is more valuable than HCl, so that evolution of HBr in this manner is a waste. If the ratio of bromine to chlorine is substantially lower than that indicated, chlorination of the bisphenoxyalkane proceeds to a substantial extent and hampers realization of the desired amount of bromination for the production of the preferred products of the invention, i.e., essentially fully or perbrominated bisphenoxy-ethane or -propane. Preferably, bromine and chlorine are used in about a 1:1 molecular ratio. Any stoichiometric excess of the bromine chloride over the bisphenoxyalkane is effective to encourage short reaction periods and complete conversion. As a rule, the excess of bromine chloride over the bisphenoxyalkane is from about 5% to about 50% molar excess.

Lewis acid catalysts in general, such as iodine, are operative in catalyzing the process. However, the desirable Lewis acid catalysts are the metal halides capable of effecting a Friedel-Crafts reaction. Of these the preferred ones are the bromides and chlorides of aluminum, iron, antimony, and mixtures thereof, antimony chloride being the most preferred. Specific examples of metal halide Lewis acid catalysts include $SbCl_3$, $SbCl_5$, $SbBr_3$, $SbBr_5$, $FeCl_3$, $FeBr_3$, $AlCl_3$, $TiCl_4$, $TiBr_4$, $SnCl_2$, $SnCl_4$, $SnBr_4$, $AlBr_3$, $BeCl_2$, $CdCl_2$, $ZnCl_2$, $BF_3$, $BCl_3$, $BBr_3$, $GaCl_3$, $ZrCl_4$, $BiCl_3$, $UCl_4$, and $SeCl_4$.

It will be noted that boron is considered as a metal in accordance with the authority "Hackh's Chemical Dictionary", Fourth Edition, 1969, page 107. It is understood that any of the indicated metals, such as iron, may be added directly to the reaction mixture in elemental form, the metal reacting with the bromine or chlorine of the bromine chloride to form the catalyst. When this procedure is followed, the amount of bromine chloride employed can be adjusted to account for the reaction. Generally it is preferred to avoid the use of iron and iron salts, since the presence of iron in many plastic compositions, with which the fire retardant product of the invention would be used, would lead to discoloration.

A catalytic amount of the catalyst is used which can be readily determined by trial and error. The amounts of catalyst and bromine chloride employed appear to be interrelated in that decreasing the amount of catalyst requires an increase in the amount of bromine chloride to obtain substantially the same amount of bromination and vice versa. However, as a general rule, the catalyst is used in an amount in the range from about 5% to about 25%, and preferably from about 15% to about 20%, by weight of the bisphenoxyalkane substrate that is employed.

Both relatively weak and relatively strong Lewis acid catalysts may be employed in the present process. The relatively weak or mild Lewis acids such as $SbCl_3$, $SbCl_5$, $SbBr_3$, $SnCl_4$ and $TiCl_4$ are preferred. However, relatively strong Lewis acids, such as $AlCl_3$, $FeCl_3$, $AlBr_3$, $FeBr_3$, and $BCl_3$ can be used if the Lewis acid is destroyed before the product is recovered from the reaction mixture. This can be effected by adding water to the mixture after the bromination step and before the product is recovered. The water destroys the effect of the strong Lewis acid catalyst. The product is ultimately recovered by distilling off the bromine chloride, organic solvent and the water where that has been added. If a strong Lewis acid is not destroyed, some of the product is converted to tarry materials during distillation. This safeguard of destroying the catalyst can be followed even where relatively weak Lewis acid catalysts are used. If water is not added to destroy the catalyst, the product can be recovered by other techniques, such as filtering the reaction mixture and washing and drying the residue.

Antimony trichloride has been found to be, generally, very satisfactory as a catalyst. Aluminum chloride is useful, and a satisfactory product can be isolated if the aluminum chloride catalyst is destroyed by the addition of water before the distillation off of excess bromine chloride.

When titanium tetrachloride and stannic chloride were employed as catalysts for the bromination of diphenoxyethane, in an amount of 18.6% of catalyst based on the diphenoxyethane, each resulted in bromination products approximating 1,2-bis(dibromophenoxy)ethane. However, these two catalysts have been found to lead to minimal production of degradation products, and they are valuable for that reason for partial brominations, although they are not as efficient as $SbCl_3$, for example, for complete bromination.

The organic solvent must dissolve the indicated components of the reaction mixture and be inert toward them. Organic solvents free of carbon to carbon unsaturation have been found suitable for this purpose and especially carbon to carbon saturated chlorinated aliphatic hydrocarbons. Carbon saturation in the solvent is needed primarily to resist halogenation. However, the solvent need not be chlorinated. Specific useful solvents include: carbon disulfide, carbon tetrachloride, chloroform, tetrachloroethane, methylene chloride, trichloroethane, dibromoethane, and the like. The solvent should be substantially anhydrous since water destroys the catalyst. As used here and in the claims, the term "solvent" includes one of the reactants itself which has the described requirements of the solvent. For example, bromine chloride in excess can itself serve as the solvent.

It is generally preferred to use chlorinated solvents in the process of the present invention, since they dissolve the Lewis acid catalyst and are relatively stable to the reaction conditions. The preferred solvents for complete bromination of the substrate are 1,1,2,2-tetrachloroethane, methylene dichloride, and 1,1,2-trichloroethane. Methylene chloride works just as well for the reaction as the most preferred solvent, 1,1,2,2-tetrachloroethane, except that there is a tendency on the part of methylene chloride to escape because of its volatility.

In carrying out the present process, the solvent is first charged to a reaction vessel, followed in any sequence by the bisphenoxyethane and Lewis acid catalyst, and finally the bromine chloride. The brominating agent may be formed in situ or just prior to introduction into the reaction vessel by metering together streams of gaseous bromine and chlorine. However, it is preferred to use preformed bromine chloride which promotes faster equilibrium and minimizes side reactions. The rate of adding bromine chloride is not critical as long as a stoichiometric excess is present at least at the end of the reaction to encourage as complete a bromination as possible. As an examle, a stoichiometric excess of bromine chloride can be added to the bisphenoxyalkane over a period of time from about 30 minutes to 4 hours.

Process conditions for the liquid phase reaction likewise are not critical with the exception that subatmospheric pressures which introduce adverse effects should not be used. Otherwise, the pressure can range from about atmospheric pressure virtually to the physical limits of the apparatus and, as a practical matter, to about 200 psig. Generally, atmospheric pressure is preferred, and higher pressures are avoided, since they can lead to operating problems. If the reaction is confined, the pressure will increase since it is autogenous. If desired, the pressure of the reaction vessel can be relieved from time to time to a minor extent by venting without affecting adversely the bromination reaction. Higher pressures tend to decrease the excess of bromine chloride needed.

Likewise, although temperature is not critical, the temperature of the process can range from about minus 10° C. to about 150° C., with temperatures from about room temperature to about 50° C. being preferred. The reaction is completed within about two hours to about to as many as about twenty hours, depending on conditions and reactants. Yields of at least 77% of the product are obtained, and yields within the range of about 93% to about 98% are frequently reached.

The class of compounds obtained as products by the present invention has been previously indicated by Formula (1). A desired class of compounds obtained by the process has the formula:

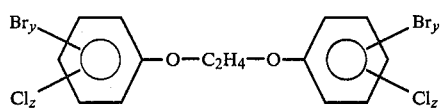

in which y is 3, 4, or 5; and z is 0, 1, or 2 and in which y and z may be the same or different. The preferred product is bis(pentabromophenoxy) ethane. The end product of the present process is a reaction mixture which, like all reaction mixtures, consists of an extremely large number of molecules, not all of which are necessarily alike. Chemical analysis of a representative sample of the reaction mass would generate numerical values for y and z that would indicate statistical average values for bromine and for chlorine respectively.

This is a difficult chemical reaction to carry out, and particularly so in good yield and with operating economy. The reaction is sensitive as to all of the compounds employed as well as to reaction conditions. For example, a change in the solvent used may require substantial changes in operating parameters to achieve equivalent results. Thus, 1,1,1-trichloroethane is useful for producing the hexabromo derivative of diphenoxyethane, but requires extreme conditions as to amount of excess bromine chloride and catalyst for producing the decabromo derivative, and/or multiple step bromination. The use of a large amount of catalyst promotes bromination, as does the use of an excess of bromine chloride.

The following Examples illustrate the invention.

EXAMPLE 1

Comparison of Different Bromination Techniques

In this example, brominated products were prepared using several different bromination techniques.

a. Reaction of Molecular Bromine with 1,2-diphenoxyethane, Fe catalyst

When 1,2-diphenoxyethane is treated with bromine using an iron catalyst and a temperature of 90° C. in the presence of an organic solvent, in the hope of producing decabromobisphenoxyethane, a yield of about 90% of pentabromophenol is obtained. Thus, when a bromination procedure is used based on the procedure published in "Bromine and Its Compounds", 2nd Ed., Teller, Academic Press, N.Y. (1966), at p. 360, for the production of pentabromotoluene, using a relatively high temperature and a strong catalyst, the following equation describes the desired (but not obtained) reaction:

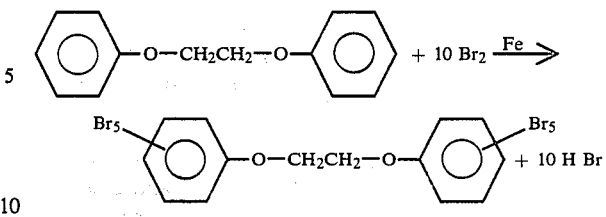

In an effort to thus produce the perbrominated bisphenoxyethane, the following reactants were employed:

| Item No. | Moles | MWt. | Wt.(g) |
| --- | --- | --- | --- |
| 1 bisphenoxyethane | 0.04 | 214. | 8.6 |
| 2 iron powder | 0.008 | 55.8 | 0.4 |
| 3 Br$_2$ | 0.48 | 159.8 | 76.7 |
| 4 Acetylene tetrachloride (ATC), for the Br$_2$ | | | 77.4 |
| 5 ATC, for the ether | | | 50.0 |

Items 1, 2 and 5 were charged into a 500 ml., 3 neck flask fitted with a mechanical stirrer, a reflux condenser, and an addition funnel. Items 3 and 4 were placed in the addition funnel. The solution in the flask was heated to 80°–90° C., and the bromine solution was added over a period of 4½ hours. The heat was then continued on the flask for another 2 hours, then 75 ml. of ATC was added and the condenser was replaced by a still head. The solvent and excess bromine were then distilled off. When no color was present in the vapor phase, the solution was cooled to 90° C. 50 ml. of 5 N of hydrochloric acid was added, and the mixture was then refluxed for 1 hour, to remove catalyst. The mixture was then cooled to room temperature, about 20° C., the supernatant liquid discarded, and the contents of the flask were filtered and washed with 5 N hydrochloric acid, then with water.

The reaction product was then dried to a constant weight at 100° C. in a circulating air oven. 35.5 g. of product were obtained having a melting point of 223°–230° C. approximately. If the entire amount of product is assumed to be pentabromophenol, the yield was 90.9%. When mixed with an equal amount of 1,2-bis(tribromophenoxy)ethane, which has a melting point of 220°–225° C., the mixture had a melting point of 194°–216° C. Based on the weight of the product and the mixed melting point, the reaction product does not appear to be 1,2-bis(tribromophenoxy)ethane, nor does it appear to be pure pentabromophenol. The theoretical yield of pure pentabromophenol would have been 39.1 g.

The combined organic layer was washed with water, then distilled until there was no solvent left. The water contained about 2 g. of a solid material.

Based on this work, it is clear that the reaction product was a mixture of many things; that while the melting point was in the range for a hexabromo product, the product was not hexabrominated; and that the reaction product did contain a substantial quantity of pentabromophenol, indicating that cleavage had occurred.

Infrared analysis confirmed that the reaction product contained pentabromophenol.

b. Reaction of Molecular Bromine with 1,2-diphenoxyethane, antimony trichloride SbCl3 catalyst When the diphenoxyethane is treated with bromine under mild conditions, that is, with antimony trichloride as the catalyst, at room temperature, the product 1,2-bis(dibromophenoxy)ethane apparently is produced. Thus, in this second reaction, using a gentler catalyst and a lower temperature, some bromination occurred without apparent cleavage of the phenoxy-to-alkylene linkage, but the bromination was relatively slight and consisted of only about two bromine atoms on each phenyl group. When the temperature for the second reaction was increased to 90° C., a complex mixture of a number of products was obtained which did contain some 1,2-bis(tribromophenoxy)ethane, along with the 1,2-bis(dibromophenoxy) ethane.

The equation for the hoped-for reaction may be written (in abbreviated form) as:

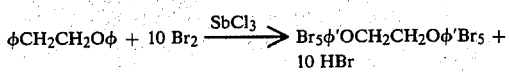

$$\phi CH_2CH_2O\phi + 10\ Br_2 \xrightarrow{SbCl_3} Br_5\phi'OCH_2CH_2O\phi'Br_5 + 10\ HBr$$

The reactants employed were:

|   |   | Moles | Wt., g. |
|---|---|---|---|
| I | φOCH2CH2O φ | 0.04 | 8.6 |
|   | ATC | — | 178.5 |
|   | SbCl3 | — | 1.7 |
| II | Br2 | 0.48 | 76.7 |
|   | ATC | — | 77.4 |

The items I were charged into a 500 ml., 3 neck flask fitted with a mechanical stirrer, an addition funnel, and a still head. The ingredients II were charged into the addition funnel, and then were added to the flask from the funnel over a period of 150 minutes at room temperature, and then stirred for 2 hours. The unreacted bromine was then distilled off along with some solvent. Water was added to the reaction mixture, and the mixture was then distilled until no more solvent was left. The reaction mixture was then cooled and filtered, then dried to a constant weight of 27.7 g. of crude product yield.

A 5 g. sample of the crude product was heated in 50 ml. of refluxing xylene and filtered hot, to produce 0.2 g. of xylene insolubles; 2.3 g. of a substance having a melting point of 220°-225° C., which dropped out of solution at room temperature; and 2.5 g. of a material which stayed in solution. Upon evaporation to constant weight, the latter material had a melting point of 135°-155° C. An attempt to obtain a sharp melting point from the 135°-155° C. portion was fruitless.

Infrared analysis indicated that the 0.2 g. portion (infusible) is inorganic; that the 2.5 g. portion (melting point 220°-225° C.) is 1,2-bis(tribromophenoxy)ethane; and that the 2.3 g. fraction (melting point 135°-155° C.) is a mixture of the hexabromo product, the tetrabromo product, and other components.

To recapitulate, it appears from the results obtained that during the room temperature phase of the reaction, the primary product obtained was the tetrabrominated product. When the temperature was raised higher, more bromine reacted, to produce some of the hexabrominated product. In both cases, the yield was relatively low. Infrared analysis did not reveal the presence of any hydroxyl group, indicating that no phenol groups had been split off.

The foregoing reaction produced a complex mixture of underbrominated (less than fully brominated) products, and demonstrates that the use of a large excess of molecular bromine does not lead to complete bromination.

The reaction was repeated, with no attempt to separate the reaction products. All of the reaction products were collected together as a single mixture. The yield of crude product was about 99% of the theoretical amount of 1,2-bis(dibromophenoxy)ethane that could be produced from the initial quantity of 8.6 g. of the 1,2-bis(phenoxy)ethane.

c. Bromination of a Partially Brominated diphenoxyethane, with a Lewis Acid Metal Salt Catalyst (i) Production of 1,2-bis(dibromophenoxy)ethane The following reactants were used:

|   | Moles | Wt., g. |
|---|---|---|
| φCH2CH2Oφ | 0.05 | 10.7 |
| Sodium acetate | 0.22 | 18.1 |
| Acetic acid |   | 180 ml. |
| Br2 | 2.2 | 35.2 |

The sodium acetate, acetic acid, and bis(phenoxy)ethane were placed in a reaction vessel, and the temperature was raised to within the range from 54° C. to 60° C. The bromine was then added gradually over a period of about 1 hour, and the vessel was permitted to stand overnight (about 16 hours), without added heat. At the end of that time, the temperature was about 40° C. Heat was applied to raise the temperature to about 100° C., and the vessel was permitted to stand for 48 hours at that temperature, to remove excess bromine.

The solution was then cooled and filtered, and the filter cake was washed with water. The washed cake was dried to a constant weight.

The filtrate was added to water, and formed a small amount of very fine powder, too fine to filter. The powder was taken up in methylene dichloride, and washed with solutions of sodium carbonate and sodium bisulfite, then dried.

The primary solid product, recovered from the acidic solution and dried, amounted to 24.5 g. having a melting point in the range from 168° to 182° C.

The residue from the methylene dichloride extract amounted to 1.5 g. and had a phenolic odor. It had a melting point of about 110° C.

If the reaction had produced the theoretical amount of 1,2-bis(dibromophenoxy)ethane, there would have been 0.05 moles of the product, or 26.5 g. The theoretical bromine content would be about 60.3%. The amount found by analysis was 59.91%. It was concluded, therefore, that the product primarily consisted of 1,2-bis(dibromophenoxy)ethane (the tetrabrominated product).

A large portion of the reaction product, 23.5 g., was recrystallized from 100 ml. of xylene. 21.3 g. were recovered of the recrystallized product.

(ii) Further Bromination in Accordance with the Invention

The following reactants were employed:

| Ingredient | Amount, g. |
| --- | --- |
| 1,2-bis(dibromophenoxy)ethane | 17.5 g. |
| SbCl$_5$ | 0.5 ml. |
| ATC | 100 ml. |
| bromine chloride solution* | 34.2 g. |

*Made up from 500 ml. of ATC, 160 g. Br$_2$, and 77.6 g. Cl$_2$.

The tetrabrominated product was the recrystallized product described immediately above. It was placed in a reaction vessel together with the antimony chloride catalyst and the solvent, and the bromine chloride solution was added gradually over a period of 17 minutes at a temperature in the range from about 23° to 26.5° C. The temperature was then raised gradually to a maximum of 41° C. for a few minutes, and the reactants were then permitted to stand over a weekend. The temperature was then raised gradually during a period of several hours, to a maximum of 72° C., the total time at a temperature above about 60° C. being over 60 hours. The solid reaction product was recovered.

The process was repeated, with the use of approximately twice as much bromine chloride solution, in a further attempt to achieve substantially complete bromination. The addition of the bromine chloride solution was made at 71° C. The reactants were then permitted to stand at room temperature for a few days. No precipitate appeared upon cooling. A solution of sodium bisulfite was added, and 4 g. of precipitate collected, having a melting point of 196°–210° C. The remainder produced a solid residue on drying of 22 g. of material having a melting point of 140°–160° C. From their melting points, it was clear that all of these materials had been brominated, but were less than fully brominated. The reason for achieving less than complete bromination is believed to have been that a relatively small amount of catalyst was used, based on substrate, i.e., 6.6% by weight.

These partially brominated products were further reacted as follows.

(iii) Preparations of Fully Brominated Products

A mixture of partially brominated products from the foregoing reactions was treated with a substantial excess of the same bromine chloride solution in the presence of antimony pentachloride, in a solution of tetrachloroethane. The reaction generated an exotherm at about 32° C., and gas passed out of the reaction solution. A precipitate appeared on the wall of the flask. After 1 hour, a small amount of ATC was added. The mixture remained too thick to stir, so that it was transferred to a larger flask and diluted with a further, substantial volume of ATC. This slurry was then heated for a few hours at about 85° C., and left to stand at room temperature for a few days. It was then heated again at 85° C. for several hours, cooled, and then filtered and washed twice with methanol. The solids were dried to a constant weight, and were found to have a melting point of 322°–324° C. The product was light brown in color.

A small specimen of this product was dissolved in refluxing mixed xylenes, cooled, filtered, and dried overnight. The melting point of the recrystallized material was 323°–324° C.

The unrecrystallized product was subjected to an analysis, to determine whether it was the decabrominated product. The analysis was as follows:

|  | % C | % H | % Br | % Cl |
| --- | --- | --- | --- | --- |
| calculated for the pure decabrominated product | 16.76 | 0.40 | 79.65 | —* |
| found by analysis | 16.91 | 0.36 | 76.82 | <0.05* |

*Analysis for a single other halogen in such a highly brominated product is difficult. The analytical error in the halogen analyses reported in this and other examples herein is believed to be on the order of about 0.4% by weight of the product analyzed.

From this work, it is concluded that the fully brominated product was produced, although there was a minor content of chlorine.

In other demonstrations of the production of fully brominated products, when the diphenoxyethane was treated in accordance with the present invention, namely, at room temperature in the presence of either antimony trichloride or aluminum trichloride, with an organic solvent having carbon to carbon saturation and containing a stoichiometric excess of bromine chloride in substantially equimolecular amounts of bromine and chlorine, yields of over 90% were obtained of 1,2-bis(pentabromophenoxy)ethane.

EXAMPLE 2

Essentially Complete Bromination of 1,2-diphenoxyethane by Bromine Chloride with an SbCl$_3$ Catalyst The following is a complete description of one form of the present process. It is a description based on laboratory experience in the practice of the process, for use in a pilot plant.

To prepare bromine chloride, an amount of 106.5 g. of tetrachloroethane as a solvent is charged into a 200 ml. flask and cooled to a temperature within the range of 0° to about 5° C. while stirring. Bromine is then added in an amount of 53.2 g. followed by an addition of 31.2 g. of chlorine via a gas sparger at the rate of 11 g. per hour.

In a reactor flask, 127.5 g. of tetrachloroethane and 8.6 g. of 1,2-diphenoxyethane are charged and dissolved with stirring. This solution is filtered to remove a small quantity of insolubles. Antimony trichloride is then added in an amount of 1.2 g., as the Lewis acid catalyst.

167.6 g. of bromine chloride solution, prepared as described, are added over a period of about three hours to the reactor flask, while maintaining the solution at a temperature of about 18° C. to about 30° C. The solution is then stirred for another three hours at room temperature.

The foregoing describes the reaction of about 0.6 moles of bromine chloride with about 0.04 moles of bis(phenoxy)ethane. As will be seen, the conditions described result in a substantial yield of the fully halogenated product, theoretically 1,2-bis(pentabromophenoxy)ethane. In practice, the product usually contains up to 1% or so of chlorine which apparently has been substituted in the phenyl ring, in place of bromine.

Two factors control the rate of addition of bromine chloride, namely, the ability to control the exothermic reaction and the need to minimize the loss of the brominating agent with escaping HCl. The bromination involves the electrophilic substitution of a bisphenoxyalkane without breaking the phenoxy-to-alkylene linkage. Bromine chloride allows the reaction to be run under relatively mild conditions (room temperature and lower) in the presence of a weak Lewis acid catalyst, such as antimony trichloride or antimony pentahalide, which do not degrade the product in boiling tetrachloroethane (147° C.). At the same time, bromine chloride offers an economic advantage over the use of bromine alone. The present process eliminates the problem of oxidizing hydrogen bromide, given off as effluent from prior brominating processes, back to bromine and then recycling bromine as the brominating agent.

Following the reaction which produces the polybrominated product, the reaction mixture is heated sufficiently to distill off excess bromine chloride together with some solvent as used for the reaction. During the distillation, the still head temperature increases gradually to that of the solvent, about 147° C. The distillation is stopped when a total of 60 ml. is accumulated in the trap. At this stage, there will be no more bromine or chlorine in the reaction vessel. The absence of red vapors in the reaction vessel or still head can be taken as the end point of the distillation. The reaction mix is then cooled to room temperature and filtered, followed by a wash of the residue with 128 g. of tetrachloroethane. The residue is then again filtered. During this operation, the solvent should be protected from water as it still contains active catalyst. The filtrates are combined and stored for future use in similar reactions.

A reactor is charged with 160 g. of water. The water is heated until it starts to distill, then the filter cake is added. The distillation is continued until no more solvent distills off. This step removes solvent, and any residual hydrochloric acid, and deactivates any residual catalyst.

The residue of these filtering steps is oven dried at about 100° C. to obtain the final product. Yields from this procedure typically range from about 92% to about 94% and higher. The product has a melting point of 312° C. to 316° C. and is a white to off-white powder in appearance. Typical volatility as determined by thermogravimetric analysis:

$T_0$: 285° C.
$T_1$: 315° C.
$T_5$: 337° C.
$T_{10}$: 342° C.
$T_{25}$: 353° C.
$T_{50}$: 361° C.

In place of the catalyst, solvent, and other reactants indicated, any of the previously disclosed corresponding components may be used.

EXAMPLE 3

Partial Bromination of 1,2-diphenoxyethane with Bromine Chloride, SbCl$_5$ Catalyst A solution was made of 65 ml. of 1,1,2,2-tetrachloroethane, 8.6 g. (0.04 mole) of diphenoxyethane and 0.25 ml. of antimony pentachloride. The solution was cooled in an ice bath and to it was added, over 30 minutes, a solution containing 38 g. of 1,1,2,2-tetrachloroethane, 19.2 g. of bromine (0.24 g. atoms), and 9.6 g. of chlorine (0.27 g. atoms). The mixture was stirred in an ice bath for 40 minutes and then for about 2½ hours at room temperature. 2 ml. of water were added. The brown color of the reaction mixture did not disappear.

The reaction mixture was filtered, and the solid filter cake was washed with methanol. Some solid material appeared in the filtrate. An attempt was made to remove the residue from the reaction vessel with water, but it solidified as with the addition of methanol. 25 ml. of water was mixed with the filtrate. The color remained. The three solid fractions were then dried separately to constant weights, respectively, and their melting points were determined. The recoveries were:

main fraction: 16.3 g.; m.p. 180° C.-200° C.
from the filtrate: less than 0.1 g.; m.p. 145° C.-180° C.
from the residue: 0.7 g.; m.p. 162° C.-200° C.

From these melting point determinations, it was clear that the product was not fully brominated.

Accordingly, the process was repeated, with the same amounts of ingredients and following the same procedure, with the exception that the amount of bromine chloride employed was increased to provide a 40% excess over the theoretical amount required for production of the hexabrominated product. Thus, the bromine chloride solution added to the reaction vessel contained 53 g. of tetrachloroethane, 26.9 g. of bromine (0.34 g. atoms), and 13.4 g. of chlorine (0.38 g. atoms).

The precipitate from this reaction was collected. It amounted to 29.4 g. of a solid material having a melting point, as determined by the capillary tube method, of 212° C.-218° C. It contained about 72.4% bromine, indicating that the product was approximately hexabrominated. The analytical method used was such that the amount specified for bromine actually is for halogen, so that some of the material reported for bromine was actually chlorine.

EXAMPLE 4

Essentially Complete Bromination of 1,2-diphenoxyethane, SbCl$_5$ Catalyst

Partially brominated products, such as those produced in Ex. 3, have been used for further bromination in accordance with the invention, to produce decabrominated products. For practical production on a substantial scale of decabrominated diphenoxyethane, however, the starting material must be diphenoxyethane. The two runs described in detail in this example make use of diphenoxyethane as the substrate for bromination.

A. First Run

In another, similar demonstration, this time of the complete bromination of 1,2-diphenoxyethane, a three-liter flask was charged with 360 ml. of tetrachloroethane and 293 g. of bromine. The flask was maintained at a temperature in the range from 0° C. to 4° C., and 153 g. of chlorine was then slowly added during a three-hour interval. The flask was also charged with 15 ml. of antimony pentachloride, and 51.6 g. of diphenoxyethane in 150 ml. of tetrachloroethane, over a period of about 30 minutes. The entire mixture was then stirred for 30 minutes on the ice bath, then left overnight at room temperature without stirring. The flask was then placed on a water bath at 70° C. for 4 hours, then left overnight again at room temperature. A precipitate formed in the flask. The reaction mixture was filtered, washed twice with tetrachloroethane, then washed twice with methanol.

The filter cake was dried and was found to have a melting point of 317°-321° C. It was then refluxed in methanol for 1 hour, filtered and dried, with a recovery of 227 g. of a colored product. This product was then refluxed in xylene for 2 hours, filtered and dried again. The product thus obtained had a melting point in the range 319°-322° C., weighed 219 g. and was colored. From its melting point, it was clear that the product was bis(pentabromophenoxy)ethane. From its high bromine content, it was anticipated that this would be a useful fire retardant additive for plastics.

B. Second Run

A solution was made by adding 432 g. (5.4 g. atoms or 2.7 moles) of bromine, 211 g. (5.9 g. atoms) of chlorine and 22 ml. of antimony pentachloride to 540 ml. of 1,1,2,2-tetrachloroethane. Another solution was made by dissolving 77.4 g. (0.36 mole) of 1,2-diphenoxyethane in 260 ml. of 1,1,2,2-tetrachloroethane. The halogen solution was cooled in an ice bath and the diphenoxyethane solution added to it over 37 minutes. The solution was then stirred 15 minutes in the ice bath, next at room temperature for two hours, and then left overnight. A precipitate formed was filtered, washed free of halogen first with 1,1,2,2-tetrachloroethane and then with methanol and finally dried. An amount of 345.7 g. of product of melting point 316°–319° C. was obtained.

This dried product was refluxed in about 2 liters of xylene for 2 hours, cooled, filtered, and dried. The melting point of the product thus obtained was 318°–321° C., and weighed 335 g.

Recognizing that the product was a mixture of several different materials, the melting point of the product, both before and after xylene purification, indicates that it was primarily the decabrominated product, 1,2-bis(pentabromophenoxy)ethane. If the recovered product is considered to be the decabromo reaction product, then the yield based on the diphenoxyethane starting material of the crude product, prior to xylene refluxing, was 95.3%, while the yield after xylene refluxing and drying was 92.4%.

EXAMPLE 5

Essentially Complete Bromination of 1,2-diphenoxyethane, AlCl$_3$ Catalyst

The amounts used in this example were 4.3 g. (0.02 mole) of diphenoxyethane, 13.7 ml. of tetrachloroethane, 0.6 g. of aluminum chloride and 0.30 mole of bromine chloride in 30 ml. of tetrachloroethane.

The bromine chloride solution was added over 1 hour, 38 minutes, to the ice cooled diphenoxyethane. The mixture was then heated for 1 hour at 40° C., after which 10 ml. of water was added and the mixture stirred at room temperature for 30 minutes (to destroy the catalyst). The excess bromine chloride was then distilled off. The solvent was then steam distilled to leave a product slurry in water. The water was made into 5 normal hydrochloric acid by adding concentrated hydrochloric acid, and the slurry refluxed for an hour, filtered and washed with water. An amount of 19.3 g. of a solid having a melting point of 308°–313° C. was obtained.

The product was recognized to be a crude product containing a mixture of several compounds. However, the melting point indicated that the primary product was the decabrominated product, 1,2-bis(pentabromophenoxy)ethane. Elemental analysis of the product indicated:

| % C | % H | % Br | % Cl |
|---|---|---|---|
| 17.09 | 0.39 | 75.11 | <0.05 |

If all of the crude product is considered to be the decabrominated product, then the yield based upon the diphenoxyethane starting reactant was about 96%.

EXAMPLE 6

Essentially Complete Bromination of 1,2bis(o-tolyloxy) ethane, SbCl$_3$ Catalyst A solution was made of 178.5 g. of 1,1,2,2-tetrachloroethane, 9.69 g. (0.04 mole) of 1,2-bis(o-tolyloxy)ethane and 1.82 g. (0.008 mole) of antimony trichloride. The solution was cooled in a water bath and to it was added over the next 120 minutes a bromine chloride solution containing 77.5 g. 1,1,2,2-tetrachloroethane, 38.4 g. of bromine (0.48 g. atom) and 17.3 g. chlorine (0.49 g. atom). The mixture was then stirred for 120 minutes at room temperature. The excess bromine chloride was distilled off and the mixture finally cooled and filtered. An amount of 24.3 g. of a dried solid product having a melting point of 218°–246° C. was recovered.

An analysis of this product indicated that it contained about 70.8% of bromine, together with about 1.6% by weight of chlorine. Total halogen analyzed at about 74.5%. The calculated, theoretical bromine content for a fully brominated product would be about 73%. A subsequent analysis of the product reported: %C, 21.57; %H, 0.94; %Br, 70.60; %Cl, 1.69.

Partly because of the low recovery of solid product, the filtrate was steam distilled using 300 ml. of water. The volume of tetrachloroethane collected was 260 ml. The residue was filtered, and a solid filter cake was recovered and dried at 75° C. to a constant weight of 7.2 g. This filter cake product had a melting point of 167° C.–182° C. Subsequent analysis indicated: %C, 19.80; %H, 0.94; %Br, 44.60; %Cl, 14.86. If it were considered to be a fully brominated product, then it, together with the solid product obtained from the initial reaction, would indicate a total yield of fully brominated product, based upon the amount of substrate 1,2-bis(o-tolyloxy)ethane employed as starting material, of slightly over 90%. However, the relatively low yield obtained of precipitated product during the initial reaction, together with its broad melting point, justifies an assumption that the two solid products recovered were not fully brominated.

Accordingly, 19 g. of the precipitate from the initial reaction was rebrominated by placing it in a reaction vessel together with tetrachloroethane and antimony chloride, then adding to the flask over the next 120 minutes a bromine chloride solution in substantial excess over the amount that would be required for essentially complete bromination. After completion of the addition of the bromine chloride, the mixture was stirred for 120 minutes at room temperature. The excess bromine chloride was then distilled off, and the mixture finally cooled, and then filtered. The filter cake was subjected to steam distillation for complete removal of the tetrachloroethane, then the mixture was again filtered. The recovered product appeared to be a completely brominated product (containing a minor amount of chlorine along with the bromine).

EXAMPLE 7

Bromination of Previously Chlorinated Substrates a. Bromination of 1,2-bis(2-chlorophenoxy)ethane, SbCl$_3$ Catalyst

The substrate for bromination, 1,2-bis(2-chlorophenoxy)ethane, in an amount of 159.7 g. (0.57 moles) was placed in a reaction flask along with 25.71 g. of SbCl$_3$ and 2,522 g. of tetrachloroethane. Over the next three hours, a solution of bromine chloride was added. The solution was made up of 1,095 g. of tetrachloroethane, 226.5 g. of bromine, and 244.6 g. of chlorine. The amount of bromine chloride employed was a 50% excess over that theoretically required for the substantially complete bromination of the substrate. Because of difficulty in stirring, approximately 1100 ml. of tetrachloroethane was added to the reaction vessel.

After the bromine chloride was added, the reaction mixture was stirred for an additional three hours, and then was permitted to stand overnight. The excess bromine chloride was then distilled off, and because of the large amount of tetrachloroethane that had been added, some of it was also removed. The reaction vessel was then left to cool overnight.

Approximately 1800 ml. of tap water was then added to the reaction vessel for steam distillation. When the steam distillation had been completed, approximately 2,350 ml. of tetrachloroethane had been collected. The reaction mixture was then cooled to room temperature, and 1,250 ml. of concentrated hydrochloric acid was added, to make the solution approximately 5 N. The solution was refluxed for one-half hour to destroy the catalyst, then cooled.

The reaction mixture was filtered to remove the solid product. The filter cake was washed three times with about 1,000 ml. of water. The product was then dried, slurried in 1,200 ml. of methanol, stirred for two hours, and filtered again. It was then placed in an oven and dried to a constant weight at 105° C.

The recovered product weighed 487.4 g. and had a melting point of 296°-304° C. The thermogravimetric analysis of the product was as follows:

$T_1$: 301° C.
$T_5$: 335° C.
$T_{10}$: 349° C.
$T_{50}$: 362° C.

An elemental analysis of the product led to the following results:

| Weight Percent Of | Theoretical | Found |
|---|---|---|
| Carbon | 18.39 | — |
| Hydrogen | 0.44 | — |
| Oxygen | 3.50 | — |
| Bromine | 69.94 | 69.17 |
| Chlorine | 7.76 | 7.86 |
| Antimony | — | less than 0.01 |

All of the foregoing results are consistent with a fully brominated product, corresponding to 1,2-bis(2-chlorotetrabromophenoxy)ethane.

b. Bromination of 1,2bis(2,4 dichlorophenoxy)ethane, SbCl₃ Catalyst

The materials used were as follows:

| Reactant | M Wt. | G. Moles | Grams |
|---|---|---|---|
| 1,2 bis(2,4-dichlorophenoxy)ethane | 352.04 | 0.60 | 211.2 |
| Br Cl (50% excess) | 277.5 | 5.4 | 1,498.5 |
| SbCl₃ | 228.13 | 0.12 | 27.3 |
| Tetrachloroethane: | 167.9 | | |
| from BrCl solution | — | | 872.1 |
| with substrate | | | 2,307.9 |
| Total | | | 3,180 |

The substrate, catalyst and solvent were added to the reaction flask and stirred. The bromine chloride solution was added gradually over a three-hour period. After the addition had been completed, the reaction mixture was stirred for an additional three hours, then left overnight. To facilitate stirring, an extra 800 ml. of tetrachloroethane was added to the reaction flask.

The excess bromine chloride was then distilled off. It amounted to approximately 1,000 ml. of bromine chloride. The reaction mixture was then cooled, and 1,500 ml. of tap water was added for steam distillation. Upon completion of the steam distillation, approximately 2,200 ml. of tetrachloroethane had been collected altogether. After cooling, 1,160 ml. of concentrated hydrochloric acid was added. The reaction mixture was refluxed for one-half hour, and after cooling, the reaction mixture was filtered. The filter cake was mixed with 1,250 ml. of methanol, with stirring for two hours, to wash the product. It was filtered again, then dried in an oven at 105° C. The recovered product had a melting point of 285° to 292° C., which corresponded closely to the melting point expected from a fully brominated product. The recovery of 475.6 g. of product would amount to a 96% by weight yield of the fully brominated product, based on the starting substrate. Data for the thermogravimetric analysis was as follows:

$T_1$: 290° C.
$T_5$: 320° C.
$T_{10}$: 334° C.
$T_{50}$: 359° C.

An elemental analysis provided the following results:

| Weight Percent Of | Theoretical | Found |
|---|---|---|
| Carbon | 20.37 | — |
| Hydrogen | 0.49 | — |
| Oxygen | 3.88 | — |
| Bromine | 58.08 | 57.79 |
| Chlorine | 17.18 | 17.08 |
| Antimony | — | less than 0.01 |

All of the foregoing results are consistent with the fully brominated product, that is, 1,2 bis(2,4 dichlorotribromophenoxy)ethane.

EXAMPLE 8

Criticality of Length of the Alkylene Bridge

A. Bromination of Diphenoxybutane, SbCl₃ Catalyst

An attempt was made to prepare the fully brominated derivative of diphenoxybutane. To this end, a solution was made of 15.6 g. of tetrachloroethane (ATC), 4.8 g. (0.02 mole) of 1,4-diphenoxybutane and 0.96 g. of antimony trichloride. To this solution was added over a period of 86 minutes a bromine chloride solution containing 48.3 g. of ATC, 24.0 g. of bromine (0.30 g-atom), and 11.2 g. of chlorine (0.32 g-atom). The mixture was then stirred for 120 minutes. Four grams of water was added and the reaction mixture was stirred for one-half hour, to destroy the catalyst. 69.0 g. of ATC was added to aid in the removal of excess BrCl. The excess bromine chloride was then distilled off. After all of the bromine chloride was removed, the solvent was removed by steam distillation.

The product was then collected. It was treated with concentrated hydrochloric acid, followed by treatment with 10% sodium hydroxide. 12.8 g. of base-soluble material was collected and identified as product 8-A-I. It had a melting point of 207°-229° C. Infrared analysis suggested that it consisted of pentabromophenol. If all of the substrate had been converted to pentabromophenol, the amount of product recovered would have represented a yield of 65.5% based on substrate.

In addition, 2.5 g. of base-insoluble material was collected and identified as product 8-A-II. It was recrystallized from xylene. It had a melting point of 200°–203° C. Elemental analysis indicated 70.6% Br and 2.6% Cl, corresponding somewhat to hexabromodiphenoxybutane (1,4-bis(tribromophenoxy)butane). The yield of this material based on substrate was 17.6%.

The very high production of pentabromophenol indicates that the substrate was subjected to substantial cleavage during this reaction. The initial hope for the bromination was that it would produce a fully brominated product. The discovery that cleavage occurred indicated that the bromination process of this invention will not be useful as a high-yield process for the bromination of diphenoxyalkanes having more than three carbons in the alkylene bridge.

Product 8-A-II was investigated further as follows. 5.2 g. of this product was treated with 200 ml. of 5% sodium hydroxide at 50° C. for 1½ hours. The mixture was then filtered, and the filter cake, which was a material insoluble in the base, was dried to a constant weight at 50° C. It is identified as product 8-A-IIa. It weighed 0.1 g., and had a melting point of about 285° C. Infrared analysis suggested the presence of inorganic materials.

The filtrate obtained was acidified to produce a white precipitate, which was dried to a constant weight at 50° C. and identified as product 8-A-IIb. This base-soluble precipitate weighed 6.2 g. and had a melting point of about 223°–235° C. Infrared analysis suggested that its major component was pentabromophenol. Carbon analysis of some of these products indicated the following:

| Product | Percent Carbon by Weight |
|---------|--------------------------|
| 8-A-I   | 19.92                    |
| 8-A-II  | 12.95                    |
| 8-A-IIb | 9.08                     |

From these data it appears that something over 41% of the ether bond was cleaved in the 1,4-diphenoxybutane, as determined by elemental analysis. If computed on the basis of the amount of material recovered as base-soluble product, and if that material is assumed to be fully brominated, then there was a 51% yield of pentabromophenol based on initial substrate. The corresponding yield of partially brominated diphenoxybutane was, as reported earlier, 17.6%. Full bromination was not achieved, it is theorized, because a phenol salt or complex forms with the catalyst and impedes the reaction.

B. Bromination of Butyl Phenyl Ether, SbCl$_3$ Catalyst

A solution was made of 172.2 g. of tetrachloroethane, 12.0 g. (0.08 mole) of butyl phenyl ether and 1.7 g. of antimony trichloride. To this solution was added over a period of 138 minutes a bromine chloride solution containing 83.8 g. of tetrachloroethane, 41.6 g. of bromine (0.52 g-atom and 19.4 g. of chlorine (0.55 g-atom). The mixture was then stirred for 150 minutes at room temperature. The excess bromine chloride was then destroyed by stirring with an aqueous solution of sulfur dioxide.

The precipitate was collected, then treated with 5 N hydrochloric acid. The product had a weight of 10.8 g. Infrared analysis strongly suggests that this product consisted of pentabromophenol. The melting point was 204°–240° C.

The liquid material, left behind after collection of the precipitate, was steam distilled and a residual product was collected. This product was treated with 5 N hydrochloric acid, and then with 10% sodium hydroxide. The product thus obtained amounted to 9.1 g. and was base-soluble. It had a melting point of 188°–238° C., and infrared analysis strongly suggested pentabromophenol.

Combining the two products provided a total weight of 19.9 g. If this entire amount represented pentabromophenol, then based upon the initial substrate material, the yield of pentabromophenol was 51% by weight.

Of the product obtained by steam distillation, 15.2 g. proved to be base-insoluble, and had a melting point of 78°–80° C. after recrystallization with isopropyl alcohol. Elemental analysis suggested it was the n-butyl pentabromophenyl ether. Assuming it to be this ether, the yield was 35%.

From the foregoing, it is clear that the linkage between the alkyl portion of the ether and the phenoxy portion of the ether has a decided tendency toward cleavage, when the alkyl group contains more than three carbons.

C. Bromination of diphenoxyhexane, SbCl$_3$ Catalyst

An attempt was made fully to brominate a different substrate, 1,6-diphenoxyhexane, while avoiding cleavage. The following reactants were employed:

| Reactant | G. -Moles | Gms. |
|----------|-----------|------|
| 1,6-diphenoxyhexane | 0.04 | 10.82 |
| bromine chloride | 0.52 | 144.25 |
| SbCl$_3$ | — | 1.7 |
| ATC |  |  |
|   from BrCl solution | — | 83.9 |
|   used with substrate | — | 172.1 |
|   total | — | 256 |

The reaction flask was charged with the substrate 1,6-diphenoxyhexane, and with 172.1 g. of ATC. The flask was cooled until an equilibrium temperature below 5° C. was obtained. At that point the antimony chloride was added, with stirring. The bromine chloride solution was then added slowly over a 2-hour period, while maintaining the temperature of the reaction flask well below 5° C. After the addition was complete, the reaction mixture was stirred for an additional 2 hours.

In order to destroy the bromine chloride, the reaction mixture was slowly poured into a beaker containing water at a temperature of about 5° C., and sulfur dioxide was bubbled through the mixture, while making sure that the temperature of the liquid did not rise above 10° C. The water and ATC layers were then separated. This involved decanting the water, then placing it in a separatory funnel and removing the ATC layer. When all of the ATC layer had been removed, the remainder was filtered. The emulsion took about 2 days for separation. After filtering, some ATC was found in the filtrate, and was combined with the original ATC layer. The filter cake was then placed in an oven at 75° C., to obtain a constant weight.

The recovered product, identified as product 8-C-I (which was the filter cake that was insoluble in water and in the ATC solvent), weighed 25.3 g. and had a melting point of 178°-184° C. Infrared analysis indicated the presence of a hydroxyl group.

The ATC layer was steam distilled, using 300 ml. of water. After removing all of the ATC, the mixture was cooled. The mixture was then filtered, and the filter cake was placed in an oven at 50° C. to obtain a constant weight. The filtrate was stored. The filter cake, identified as product 8-C-II, weighed 9.8 g. and had a melting point of 175°-218° C. Infrared analysis indicated the presence of a hydroxyl group.

In view of the presence of the hydroxyl group in product 8-C-II, that product was extracted by treating it with 185 ml. of 5% sodium hydroxide for 1½ hours at about 50° C., and was then filtered. The filter cake, which was base-insoluble, was placed in an oven at 55° C. to obtain constant weight. This product was identified as product 8-C-III. The filtrate was acidified to precipitate out any base-soluble material. A precipitate appeared, was collected, and was placed in an oven at 55° C. to obtain a constant weight; it was identified as product 8-C-IV.

Product 8-C-III weighed 2.0 g. and had a melting point of 162°-172° C. Infrared analysis indicated the absence of any hydroxyl group in this base-insoluble material.

Product 8-C-IV, the base-soluble material, weighed 5.6 g. and had a melting point of 218°-235° C. Infrared analysis indicated that this material probably was pentabromophenol.

Product 8-C-I was further investigated in the following way. 23.84 g. of this product was treated with about 500 ml. of 5% sodium hydroxide for 1½ hours at about 50° C., to remove any base-soluble material. The solution was then filtered. The filter cake, of base-insoluble material, was dried to constant weight at 50° C. It was identified as product 8-C-Ia. It weighed 13.0 g., and had a melting point of 216°-223° C. Infrared analysis failed to indicate the presence of a hydroxyl group.

The filtrate was acidified with hydrochloric acid, to produce a white precipitate. Precipitate was collected and dried to a constant weight of 50° C. It was identified as product 8-C-Ib.

In order to permit an estimate to be made of the extent of cleavage of the ether bond, a carbon analysis was run on certain of the products as follows:

| Product | Percent Carbon by Weight |
| --- | --- |
| 8-C-III | 22.11% |
| 8-C-IV | 13.13% |
| 8-C-Ia | 20.23% |
| 8-C-Ib | 9.05% |

These figures clearly demonstrate that the base-soluble products are phenolic. Coupled with the infrared analysis indications, the base-soluble product fractions appear to be pentabromophenol, in admixture with other materials of lower carbon content, possibly brominated materials derived from the alkylene bridge.

From the available data it appears that about 36% of the ether bonds cleaved in this attempt at bromination of 1,6-diphenoxyhexane, calculated on the basis of elemental analysis. If calculated on the basis of the amount of material recovered as base-soluble product, and if assumed to be fully brominated, then the figure is a 52.5% yield of pentabromophenol based on initial substrate.

Comment on Example 8

From these experiments several observations and conclusions are possible. The purpose of the experiments described in this example was to produce a fully brominated compound. Chemical removal of bromine was employed in 8B and 8C to keep cleavage at a minimum. Nevertheless, cleavage still occurred, at a rate overall greater than 50%, taking all of the data into account.

Because of the rate at which cleavage occurs, the process of this invention does not appear to offer a high yield way to make fully brominated compounds when the alkylene bridge contains four or more carbon atoms, since the main product obtained is brominated phenol, mixed with brominated material derived from the alkylene bridge.

Attempts were made to produce pentabromophenol from phenol by the process of the present invention. The usual result was a pentahalide mixture that contained, on a statistical average, 3.5 atoms of bromine and 1.5 atoms of chloride per molecule of pentahalophenol.

EXAMPLE 9

A. Pilot Plant Scale Bromination to Produce 1,2-bis(pentabromophenoxy)ethane

The manner in which the reaction is carried out on a large scale must be adjusted to accomodate the features of the equipment that is available. In one preferred embodiment of the invention, the process is practiced on a pilot plant scale.

Each of the reactors employed is glass-lined and is provided with an agitator, and is jacketed. All of the interconnecting lines in the production equipment are either glass-lined or lined with an inert plastic material. However, the tank for handling the product may be equipped with stainless steel lines and valves.

Appropriate safety precautions must be taken, because of the toxic nature of several of the reactants.

A 50-gallon reactor and a 75-gallon reactor are employed. The 50-gallon reactor is placed under vacuum, and 193 lbs. of tetrachloroethane (ATC) is drawn into the reactor. Next, 135.3 lbs. of bromine is drawn into the reactor. Cooling fluid is then circulated through the reactor jacket, to keep the contents of the reactor at a temperature in the range from about 5°-10° C. during the addition of chlorine. Chlorine is then slowly added to the reactor at a rate such that the internal pressure in the reactor does not exceed 10 psi and the temperature does not rise above 10° C. 54.9 lbs. of chlorine gas is added in this fashion. The average analysis of the contents of the reactor, at this point, should indicate the presence by weight of about 50.37% of the solvent ATC, about 35.31% bromine, and about 14.3% chlorine. This is a target analysis and if it is not achieved, either more chlorine or more bromine may be added to achieve it.

A 75-gallon reactor is used for the next step. The reactor is evacuated and 445 lbs. of tetrachloroethane (ATC) are drawn into the reactor. Nitrogen is then admitted to the reactor to break the vacuum. 27.9 lbs. of diphenoxyethane is then added to the reactor, and the contents of the reactor are mixed for about 15 minutes. Finally, 5.6 lbs. of antimony trichloride are added to the reactor, and mixing is continued for 5 to 10 minutes.

The vents from the 75-gallon reactor, containing the substrate diphenoxyethane, are adjusted to permit taking off hydrogen chloride as it evolves in the subsequent reaction, together with any gaseous chlorine and bromine that may escape. Preferably, the gas vent leads to a condenser for recovery of any escaping bromine.

At this point, the addition of the bromine chloride solution from the 50-gallon reactor is commenced, by transferring it gradually into the 75-gallon reactor containing the substrate. The temperature on the larger reactor is kept below about 15° C. during the addition by appropriate heat exchange, since the reaction is exothermic. If red vapors appear in the reactor during the reaction, it is an indication that the addition of bromine chloride is being made too rapidly. Generally all of the bromine chloride solution can be transferred to the reactor containing the substrate in about 1 hour.

After about 25% of the bromine chloride solution is added, precipitation will generally begin. As soon as the precipitation begins, the temperature on the reactor can be permitted to rise to about 25° C.–38° C. After about ¾ of the bromine chloride solution has been added, the precipitate may begin to adhere to the wall of the reactor, and the agitation may not be very effective. If it is observed that the agitator is operating but there is little or no circulation in the reactor, the addition of the bromine chloride solution may be interrupted until the slurry becomes sufficiently fluid for circulation to begin again.

After all of the bromine chloride has been added, the contents of the reactor are permitted to stand at a temperature slightly above room temperature, for about 1 hour, while agitation is continued.

Thereafter, the reactor is heated slowly, preferably by circulating steam through the reactor jacket, until the contents of the reactor attain a temperature of about 160° C. Vapor begins to be evolved at a temperature up to about 140° C. This heating is continued until all of the excess bromine chloride has distilled off, with care being exercised, to the extent possible, to avoid distillation of the solvent. The distillation is accompanied by red vapors, and when such vapors are no longer observed, removal of the bromine chloride can be considered to be completed.

Generally, during the heating cycle to drive off bromine chloride, the progress of the distillation can be judged by the vapor temperature. When the vapor temperature is in the range from 25° C. to 50° C., the evolved gases are primarily hydrogen chloride and chlorine. When the vapor temperature is in the range from 50° C. to 82° C., the evolved vapors are primarily bromine and are red. When the vapor temperature is from about 82° C. to about 160° C., the evolved gases are primarily the solvent, ATC, with traces of bromine that gradually disappear.

During the removal of excess bromine chloride, if the slurry becomes so thick that it does not circulate as it is agitated, then an additional quantity of solvent may be added, such as, for example, 100 lbs.

After removal of the excess bromine chloride has been completed, the slurry from the reactor is filtered on a rotary vacuum filter, with care being taken to exhaust the filters. The filter cake is rinsed with about 2 lbs. of the solvent, ATC, for each pound of filter cake.

The filter cake is then transferred into a 300-gallon tank containing about 150 gallons of water. The cake and water are thoroughly mixed, and the tank is then heated to effect steam distillation for the removal of solvent. After all of the solvent has been removed, the contents of the tank are slowly cooled down to about 27° C. The contents of the tank are then filtered to remove liquid, then dried under a vacuum of about 28 inches of mercury at about 65° C.

The mother liquor separated from the solid product during rotary vacuum filtration is subjected to a distillation operation if necessary to insure that it is anhydrous, and is then set aside for reuse. Its content of the solvent, ATC, and of the catalyst, antimony trichloride, are valuable and are suitable for use in another run of the process.

The recovered product from this process should be about 125 lbs. of dry material having a melting point of about 312° C. minimum. It should be white and have a bromine content of 77% minimum. Generally the bromine content will be higher, and usually the product contains a small amount of chlorine in addition to the bromine. The amount of chlorine is generally less than 1% by weight of the product, but may be as much as 2%. Theoretically, the bromine content of a diphenoxyethane that has been brominated to contain 9 bromine atoms per molecule, with a molecular weight of approximately 924, would be about 77.5%, whereas a fully brominated diphenoxyethane, containing 10 bromine atoms per molecule, would have a molecular weight of 1,003 and a bromine content of about 79.9% by weight. Since the presence of some chlorine in the reaction product is difficult to avoid, a specification of a bromine content about 77% by weight or higher of the product that is recovered is considered adequate to insure the production of a product having excellent fire retardant properties.

Since the chlorine content of the product is generally from about 1% to about 1.5%, the molecular weight of the product is actually about 97% of the 1,003 molecular weight of the decabrominated product. Accordingly, a specification of 77% by weight of bromine in the reaction product actually indicates a fully halogenated product, that closely approaches being a decabrominated product.

B. Representative Pilot Plant Production Run

The initial run that is described in this example is the first in a series of runs, each carried out generally in accordance with the procedure of Example 9A. The series was designed to see if it would prove to be feasible to recycle bromine chloride recovered from a trap to subsequent production runs as a matter of economy, and whether it would be feasible to recycle mother liquor, obtained from final product filtration and containing some dissolved brominated reaction products and catalyst, directly to the reaction.

This series of runs was also designed to try to minimize catalyst losses and to determine whether iron is picked up during the process so that it appears in the product. The presence of iron in the product is undesirable for a product intended for fire retardant applications in several plastic compositions, since iron seems to promote discoloration.

A bromine chloride solution was made up from 193 lbs. of ATC as the solvent, 135.3 lbs. of bromine, and 54.9 lbs. of chlorine. The maximum temperature during addition of the chlorine was 10° C., and the time taken was 3½ hours.

The substrate solution was made up from 27.9 lbs. of diphenoxyethane in 445 lbs. of the solvent, ATC. 5.6 lbs. of antimony trichloride was added, which amounts to 20% by weight based on the diphenoxyethane.

The bromine chloride solution was added to the reactor containing the substrate solution over a period of 1¼ hours. The maximum temperature attained during addition was about 44° C. After the addition had been completed, the reaction mixture was held in the reactor for 1 hour at a temperature in the range from about 27° C. to about 35° C.

The reaction mixture was then heated to distill off excess bromine chloride. This operation required 2¼ hours. The weight of bromine chloride recovered from the distillation was 100 lbs.

During the reaction, the reactor was vented to a trap, and 110 lbs. of the solvent ATC were recovered from the trap. Since this probably included bromine chloride, the bromine chloride recovered from the distillation step was combined with the ATC from the trap, for a total of 210 lbs. This was analyzed and proved to contain 11.5% by weight of bromine, and 0.42% by weight of chlorine.

The excess of bromine used for the reaction, by weight, was calculated based on chlorine, since chlorine was the limiting reactant. On this basis, the excess of bromine was 29.83%. The initial excess of chlorine was 19.0%.

The material remaining after distillation off of the excess bromine chloride was filtered, and the filter cake was washed with 209 lbs. of the solvent ATC. The washed filter cake was stirred into 150 gallons of water, then subjected to steam distillation, which required about 5 hours. The residue was then filtered to separate mother liquor and dried to a constant weight at about 72° C.

The recovered finished product amounted to 112 lbs. containing 77.0% bromine and 1.4% chlorine. If all 112 lbs. are considered to be the decabrominated product, then the yield obtained, based upon the amount of substrate employed, was about 85.75%. This product was essentially free from antimony and contained about 57 ppm of iron. When subjected to thermogravimetric analysis, the following data was obtained:

$T_1$: 330° C.

$T_{10}$: 350° C.

$T_{50}$: 365° C. The melting point as measured by differential scanning colorimetry was 304° C., with a melting point range of 290°–315° C.

Following essentially the same procedure, two additional runs were made as a part of this series. For the second run, the recovered bromine chloride and the mother liquor from the previous run were used as an economy measure. The mother liquor contained some brominated materials, but primarily was of value for its content of solvent and catalyst. The data for these sequential runs is as follows, on a weight basis and in pounds, where not otherwise specified:

|  | Run 9-2 | Run 9-3 |
|---|---|---|
| Bromine Chloride Makeup |  |  |
| ATC | 210 | 210 |
| Recovered Bromine | 24 | 24.9 |
| New Bromine | 111.2 | 110.4 |
| Total Bromine | 135.3 | 135.3 |
| Recovered Chlorine | 1.1 | 4.5 |
| New Chlorine | 53.8 | 50.4 |
| Total Chlorine | 54.9 | 54.9 |
| Max. Temp. During Addition | 10° C. | 10° C. |
| Time for Cl₂ Addition | 4 hrs. | 4 hrs. |
| Substrate Makeup |  |  |
| Mother Liquor Charged | 575 | 528 |
| Recycled Distilled ATC | 120 | 83 |

|  | Run 9-2 | Run 9-3 |
|---|---|---|
| Total ATC | 455 | 445 |
| Diphenoxyethane | 27.9 | 27.9 |
| Recovered SbCl₃ | 4.6 | 3.4 |
| Fresh SbCl₃ | 1.0 | 2.2 |
| Total SbCl₃ | 5.6 | 5.6 |
| %SbCl₃ on substrate | 20.0 | 20.0 |
| Reaction |  |  |
| Addition Time | 1¼ hrs. | 1¼ hrs. |
| Max. Temp. During Add. | 43.3° C. | 43.3° C. |
| Holding Time | 1 hr. | 1 hr. |
| Holding Temp. | 29°–35° C. | 29°–35° C. |
| Temp. Range Add/Hold | 29°–43.3° C. | 29°–43.3° C. |
| Time for DWT Excess | 2 hrs. | 2¼ hrs. |
| Wt. Dist. BrCl | 100 | 165 |

|  | Run 9B-2 | Run 9B-3 |
|---|---|---|
| Traps |  |  |
| ATC initial | 110 | 110 |
| Total at the end | 210 | 275 |
| Analysis % Br | 11.9% | 10.3% |
| % Cl | 2.2% | 0.8% |
| Start % Excess Bromine | 29.83% | 29.83% |
| Start % Excess Chlorine | 19.0% | 19.0% |
| Recovery, % Br by chemical analysis | 80.6% | 91.6% |
| Recovery, % Cl by chemical analysis | 52.0% | 24.9% |
| Product Recovery |  |  |
| ATC Used for Washing | 171 | 175 |
| Mother Liquor Wt. | 528 | 372 |
| Wet ATC during steam distillation | 228 | 222 |
| Amount of water for steam dist. | 150 gal. | 150 gal. |
| Time for Steam Distillation | 5 hrs. | 5 hrs. |
| Time for Filtration | 6 hrs. | 6 hrs. |
| Drying Temp. | 71° C. | 71° C. |
| Drying Vac. | 22" vac | 22" vac |
| Moisture Water, Wet Cake | 60% | 60% |
| Finished Product |  |  |
| Wt. | 119 lbs. | 126.5 lbs. |
| Yield | 91.5% | 97.1% |
| % Bromine | 77.2% | 76.3% |
| % Chlorine | 1.3% | 1.4% |
| Fe PPM | 69 | 136 |
| % Volatile | 0.06% | 0.25% |
| TGA $T_1$ | 305° C. | 200° C. |
| $T_{10}$ | 353° C. | 353° C. |
| $T_{50}$ | 366° C. | 367° C. |
| DSC MP | 295° C. | 300° C. |
| DSC MP Range | 275°–308° C. | 280°–314° C. |
| Vis MP Range | 306°–315° C. | 295°–311° C. |

EXAMPLE 10

Essentially Complete Bromination of 1,3-Diphenoxypropane, SbCl₃ Catalyst

The following materials were employed in this laboratory scale demonstration of the invention:

| Materials | Moles | Grams | %, based on substrate |
|---|---|---|---|
| 1,3-diphenoxy-propane (substrate) | 0.04 | 9.1 | — |
| SbCl₃ | 0.0079 | 1.80 | 19.8 |
| BrCl | 0.60 | 166.4 | 50% excess |
| ATC |  |  |  |
| -with BrCl | — | 96.9 | — |
| -with substrate | — | 162.9 | — |
| -Total | — | 259.8 | — |

Complete bromination, with 100% theoretical yield, would produce 0.04 moles, or 40.7 g., of decabromodiphenoxypropane.

In this demonstration of the reaction of the invention, the soluble and insoluble products were recovered, and careful observations were made. The purpose was to ascertain the extent of any cleavage that occurred, and the identity and extent of bromination of each product. Generally, solubility in base in an indication that the product is phenolic.

A reaction flask was charged with the ATC for the substrate, the $SbCl_3$, and the substrate, to form a solution. The flask was placed in a cold bath, and the bromine chloride solution was slowly added over the next 143 minutes. During the addition the reaction mixture thickened, and the flask was removed from the water bath. The reaction mixture was then stirred for 2 hours. Excess bromine was then destroyed by slowly pouring the reaction mixture into chilled water at 5° C., with $SO_2$ bubbling through it.

After settling, the water layer was removed by decanting, and the solid product was filtered. The water and filtrate were set aside for further treatment, to recover any product soluble in ATC. The filter cake was then dried in an oven at 90° C. The dry product, 10-A, weighed 32.5 g., m.p. 235° C.–244° C.

The filtrate consisted of ATC and water. It was separated into two portions, and the water portion was combined with the water decanted and earlier set aside, to a combined weight of 1712 g. When acidified to 5 N HCl, a clear solution formed, separate from an ATC layer. The acidified layer was discarded, and the ATC layer, 519.4 g., was set aside.

The dry product, 10-A, was treated with 200 ml. of 5 N HCl at 50° C. for ½ hour. It was then cooled to room temperature and filtered. The yellow filtrate was discarded. The filter cake was dried at 100° C., to provide 30.8 g. of product 10-B, m.p. 240° C.–247° C. Elemental analysis indicated: % C, 18.09; % H, 0.58; % Br, 75.78; % Cl, 0.30; % Sb, 0.025.

The product 10-B was treated with 200 ml. of 10% NaOh at 50° C. for 1 hour. It was then cooled to room temperature, and the mixture was filtered. The filter cake was dried in an oven at 100° C. The dry cake, 10-C, weighed 30.5 g., m.p. 240° C.–248° C.

Infrared analyses indicated that products 10-A and 10-C contained no observable brominated phenol.

Elemental analysis of product 10-C, based on an average of two values for each reported figure, indicated bromine, 75.80%; chlorine, 1.78%; and antimony, 0.10%. This compares with theoretical values for the decabrominated derivative of 17.71% carbon; 0.59% hydrogen; 3.14% oxygen; and 78.55% bromine. If all of the halogen found by elemental analysis had been bromine, the percentage of bromine in product 10-C would have been 79.81% by weight. This compares closely with the theoretical figure of 78.55% by weight.

Assuming the principal product, 10-C, to be the decabrominated derivative, the yield (31.5 g.) based on substrate was 77.4%, melting point, 240°–248° C.

The filtrate was then acidified to pH 1 with concentrated HCl. A trace of a precipitate appeared. The amount was insignificant, and the filtrate was thereupon discarded.

The ATC layer that had been set aside was steam distilled, using 250 ml. of tap water. During the steam distillation, 318 ml. of ATC was removed. Following the steam distillation, the slurry product was filtered. The filtrate, which was only water, was discarded. The filter cake was placed in an oven at 50° C., to dry. The dried solid product weighed 4.7 g., m.p. 72°–95° C. This solid material was then treated with 100 ml. of 10% NaOh at 50° C. for 1 hour. The mixture was then cooled to room temperature and filtered. The filter cake was again dried in an oven at 50° C., to form product 10-D. The filtrate weighted 176.2 g. It was acidifed to pH 1 with concentrated HCl. A precipitate appeared. The mixture was then filtered. The filter cake was dried in an oven at 50° C., to form product 10-E, and the acidified filtrate was discarded.

The filter cake, 10-D, weighed 4.3 g., m.p. 90°–160° C. Elemental analysis: % C, 19.34; % H, 1,00; % Br, 63.92; % Cl, 5.84; % Sb, 0.004. The filter cake 10E weighed 0.9 g., m.p. 176°–203° C. Elemental analysis: %, C, 18.34; % H, 0.35; % Br, 55.34; % Cl, 15.04; % Sb, 4 ppm. Both of these products were subjected to infrared analysis and to nuclear magnetic resonance analysis.

The observed characteristics of the ATC-soluble, base-insoluble fraction, product 10-D, indicate that it is underbrominated substrate, or partially degraded substrate, or a mixture of both.

The properties of the ATC-soluble, base-soluble, acid-insoluble fraction, product 10-E, indicate that this product is phenolic. While it appeared to be less than fully brominated, assuming it to be tetrabromophenol, then the amount recovered would be 0.0022 moles of this phenol, as compared with 0.08 moles of substrate at the beginning of the reaction. Yield based on this phenol would therefore be something on the order of 2.75%. Elemental analysis indicated that the brominated phenol formed accounted for about 2.4% of the total carbon present.

In a somewhat similar demonstration of the process with the same substrate, a slightly lower yield of fully brominated product was obtained. It had a melting point of 244°–246° C., and elemental analysis reported the following: 75.3% bromine, 2.28% chlorine; 0.10% antimony. Had the chlorine in the product been bromine, the bromine content would have been 80.46%, which is about 1.91% above theory. While the amount of phenol in the product can only be calculated or estimated on a very rough basis, it appeared to be on the order of 5%. A subsequent elemental analysis reported: % C, 17.81; % H, 0.58; % Br, 76.42; % Cl, 0.12; % Sb, 0.058.

It can be concluded, therefore, that the process of the invention is effective for producing fully halogenated products, containing primarily bromine, of diphenoxypropane and of substituted diphenoxypropanes, but that the substrate is subject to a minor amount of cleavage with the production of phenols or other degradation products, so that the reaction is not as efficient as is the case where the substrate is diphenoxyethane or a substituted diphenoxyethane.

Fully brominated diphenoxypropane has properties that make it very desirable as a fire retardant additive for thermoplastic resins.

EXAMPLE 11

Bromination of Anisole

While prior art techniques for brominating anisole generally resulted in either little bromination, or cleavage, or both, anisole can be polybrominated in accordance with this invention to whatever degree of bromination is desired, in good yield, and essentially without cleavage.

Thus, anisole can be reacted in the laboratory with bromine chloride having a molar ratio of bromine to chlorine of 1 to 1.2, at 50% molar excess, at room temperature, in the presence of about 15%–20% by weight SbCl$_3$ based on anisole, allowing 3 hours for the addition and 3 hours with agitation for completion of the reaction.

In one such run, 8.65 g. (0.08 moles) of anisole in 140.2 g. ATC was treated with 144.8 g. of bromine chloride solution made up of 28.7% Br, 13.4% Cl, and 57.9% ATC (0.52 moles BrCl), in the presence of 1.7 g. of SbCl$_3$. The recovered product weighed 40.2 g. (0.08 moles, if pentabromoanisole).

The product apparently was pentabrominated anisole and was recovered in excellent yield, having after recrystallization from xylene a m.p. of 176°–180° C., and $T_1=153°$ C., $T_{10}=204°$ C., and $T_{50}=246°$ C.

The dibrominated and tribrominated products are also easily produced by modifying the reaction conditions, such as the amount of bromine chloride or catalyst employed, or both.

EXAMPLE 12

A Preferred Laboratory Mode

Process for the Preparation of 1,2-Bis(pentabromophenoxy) ethane by the Reaction of Bromine Chloride on 1,2-Diphenoxyethane Equation:

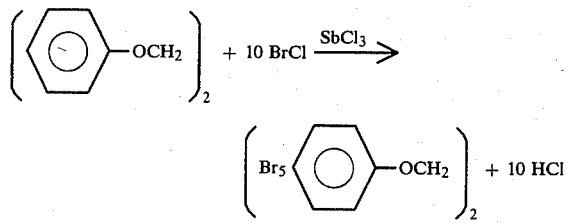

Procedure:

1. Charge 101.5 g. of tetrachloroethane into a 200 ml. flask and cool to 0°–5° C. while stirring. Acid 62.9 g. bromine. Add 25.6 g. chlorine via a gas sparger at the rate of 11 g./hour. Analyze.
2. Charge 183.1 g. of tetrachloroethane and 8.6 g. of 1,2-diphenoxyethane into a 500 ml. reactor flask. Add 1.7 g. antimony trichloride and dissolve with stirring.
3. Charge 48 g. tetrachloroethane into a trap and cool to 0°–3° C.
4. Add to the reactor 136.5 g. of the bromine chloride solution prepared in 1 over a period of 3 hours, maintaining a temperature of 18°–30° C. Stir at room temperature for 3 hours.
5. Heat the reaction mixture in order to distill the excess bromine chloride into the trap, together with some solvent. The still head temperature increases gradually to that of the solvent (147° C.). The distillation is stopped when a total of 60 ml. is in the trap. At this stage there should be no more bromine or chlorine in the reactor. The absence of red vapors in the reactor or still head is taken as the end point.
6. Filter. Wash with 128 g. of tetrachloroethane. The combined filtrates are stored.
7. Charge 160 g. water into reactor. Gradually add the filter cake into the reactor with stirring. Heat until all of the solvent azeotropes off.
8. Filter and oven dry at 100° C. and break up lumps.
9. Separate and dry tetrachloroethane from step 7 for reuse.
10. Charge combined filtrates from step 6 into reactor (after removal of residual water from the reactor). Distill until 183.1 g. of tetrachloroethane remain in reactor.
11. The recovered bromine chloride from step 5 is added to that remaining from step 1. The combined solution is analyzed. The necessary tetrachloroethane, bromine and chlorine is added, as in step 1, to give a solution of comparable concentration and bromine to chlorine ratio.
12. Charge 8.6 g. of 1,2-diphenoxyethane and make up antimony trichloride.
13. Repeat sequence starting from step 3.
14. Product:
    Yields: 36.6–37.7 g. (91%–94%)
    Melting Point: Minimum 310° C.
    Bromine: Minimum 77%

General Comments With Respect to the Brominated Products Produced

The brominated products produced by the process of this invention are generally useful as fire retardant additives for plastic material.

In particular, the fully halogenated products produced by the bromination of diphenoxyethane are fire retardant additives that are useful in a broad range of thermoplastics, with particular utility in high impact polystyrene and in ABS resins. Efficiency as a fire retardant additive is derived from the high bromine content, that is, 77% or more by weight. The fully brominated diphenoxyethane derivatives exhibit excellent thermal stability which is typical of most aromatic bromine-containing additives, and exhibit very low vapor pressure even at elevated temperatures. Unlike most aromatic bromine-containing additives currently employed as fire retardants, the fully brominated diphenoxyethane possesses outstanding light stability. This unique property greatly broadens the scope of applications in which the product can be employed.

The use of fully brominated diphenoxyethane, at additive levels required to produce good fire retardance, has a negligible effect on most resin properties. Most properties including heat distortion, tensile strength, and flexural strength, are maintained or, in many cases, are actually improved. This is particularly true of the heat distortion temperature. As might be expected, impact resistance shows varying degrees of decline depending on the nature of the resin employed. However, the impact retention of fully brominated diphenoxyethane, produced in accordance with the present invention, is at least comparable to that of leading commercial additives such as, for example, decabromodiphenyl oxide.

Fully brominated diphenoxyethane, produced in accordance with the present invention, is rated as nontoxic based on studies to determine its acute oral, dermal, and inhalation toxicities. It is classified as a nonirritant in standard eye irritation studies. As produced in the pilot plant, it typically contains 0.25% to 0.38% antimony, from the catalyst.

In appearance, fully brominated diphenoxyethane produced in accordance with the present invention is a free-flowing white to off-white powder, containing 77% or more bromine by weight. The melting point typically is in the range from 313° C. to 318° C. The content of water, as determined by the Karl Fischer method, is less than 0.1%. The product has virtually no solubility in water, and very slight solubility in organic solvents. The decomposition temperature (DSC) is about 390° C. Volatility, as determined by thermogravimetric analysis, can be expressed as follows in terms of percent weight loss, while undergoing a temperature increase of 10° C. per minute:
   1% loss: 315° C.
   10% loss: 335° C.
   50% loss: 355° C.

While fully brominated diphenoxyethane, produced in accordance with the present invention, represents the preferred product produced in accordance with the invention, and is believed to be superior in its properties with respect to fire retardance in most plastic materials, the brominated products that are fully substituted but that contain substituents other than bromine, such as, for example, the products of Examples 6, 7 and 8, are also useful as fire retardant additives.

CONCLUSION

When the process of this invention is used to perbrominate diphenoxyethane, for example, the reaction mixture that is obtained includes a major amount of the decabrominated product. The presence of up to about 1.6% by weight of chlorine, however, indicates that there are chloro-substituted molecules present. The amount will depend upon reaction conditions. For fire retardant applications, where the amount of additive used is based upon its bromine content, the purer the product, the better, in general.

To review the process conditions preferred, the temperature at which bromine chloride is prepared, by the addition of chlorine to a solution of bromine, preferably is kept at 0°-5° C., to control the exotherm. A molar ratio of bromine to chlorine in the bromine chloride solution of 1 to 1.2 is useful for laboratory-scale preparations, but a lower ratio such as 1.0 to 0.92 was found to be useful to control pressure build-up in pilot plant operations where better agitation was available. Generally a 50% molar excess of bromine over theoretical is useful, but less may be used if the available equipment lends itself to reaction efficiency, or if a large amount of catalyst is employed.

The amount of catalyst based on the substrate diphenoxyethane is preferably about 19.8% by weight of the substrate when the catalyst is SbCl$_3$. The practical minimum for operating efficiency is about 15%. More than 25% can be used but without economic advantage. An increased amount of catalyst can be used to offset a decreased excess of bromine.

The time required for addition of the bromine chloride to the substrate, and the subsequent time required to insure completion of the reaction, depend on equipment efficiency, amount of catalyst, temperature, and the like. In the laboratory, three hours addition time and three hours hold time were often used. In the pilot plant, using submerged addition of bromine chloride and good agitation, one hour of addition time and one hour of hold time have been satisfactory.

The amount of solvent used is a matter for selection. The least amount necessary is good for economics.

The best mode for practicing the process on a laboratory scale, for producing decabromodiphenoxyethane, utilizes about 15% to about 20% catalyst, preferably SbCl$_3$, by weight based on the diphenoxyethane substrate, and from 30% to 50% excess BrCl over the stoichiometric amount, at room temperature and pressure, with about 3 hours addition time and about 3 hours of agitated hold time, prior to recovery of the product. Tetrachloroethane is the preferred solvent, the preferred amount being 160 ml. for each 0.04 mole of the substrate. The amount used can be selected to facilitate agitation and for economy, since at least with ATC, the amount of solvent beyond that necessary for ease of agitation has little or no effect on yield of product.

There are some indications that higher bromine content and higher yield can be obtained when the process is practiced by forming a solution in the reaction vessel of the substrate and solvent, then adding to the reaction vessel over a period of time a second solution containing bromine chloride and the catalyst. The work done on this to date has been limited. It is theorized that when the catalyst is in the same solution as the substrate, it may form a complex with the ether linkage, and thus be diminished in its effectiveness.

The best known mode of practicing the process on a pilot plant or other scale, where good agitation and equipment is available, is described in Example 9, where recovered mother liquor and trapped bromine and chlorine are recycled.

While the invention has been disclosed herein by reference to the details of several preferred embodiments thereof, it is to be understood that such disclosure is intended in an illustrative rather than a limiting sense and it is contemplated that other modifications of the process of the invention will readily occur to those skilled in the art, within the spirit of the invention and the scope of the appended claims.

I claim:

1. A process for polybrominating a bis(phenoxy) alkane that has two or three carbon atoms in its alkane moiety, to substitute at least three bromines on each of the aromatic rings of said bis(phenoxy) alkane, without substantial cleavage of either phenoxy-to-alkylene linkage, comprising reacting at a temperature of about minus 10° C. to about 150° C. the bisphenoxyalkane with an amount of bromine chloride that is in stoichiometric excess of that required for substantially complete bromination, in the presence of a catalytic amount of a metal halide Lewis acid catalyst of at least 5% by weight based on the bis(phenoxy) alkane, and a chemically inert organic solvent adapted to dissolve all of said reactants and catalyst, under substantially anhydrous conditions, to form a product having the formula:

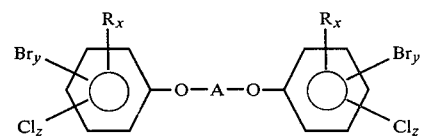

in which A is alkylene of two or three carbon atoms; R is alkyl up to and including four carbon atoms; x is 0, 1 or 2; y is 3, 4 or 5; and z is 0, 1 or 2 and in which the R, x, y, and z for the respective rings may be the same or different.

2. The process of claim 1 in which said Lewis acid catalyst is selected from the bromides and chlorides of aluminum, iron, antimony, and mixtures thereof.

3. The process of claim 1 in which said Lewis acid catalyst is a metal halide selected from the group consisting of SbCl₃, SbCl₅, FeCl₃, and AlCl₃.

4. The process of claim 1 in which said chemically inert organic solvent is a chlorinated aliphatic hydrocarbon having carbon to carbon saturation.

5. The process of claim 1 in which said chemically inert organic solvent is selected from the group consisting of carbon disulfide, carbon tetrachloride, chloroform, tetrachloroethane, methylene chloride, trichloroethane, and dibromoethane.

6. The process of claim 1 in which said reaction is carried out at atmospheric pressure.

7. The process of claim 1 in which said reaction provides a yield of at least 77% of said product.

8. The process of claim 1 in which said product is fully halogenated bis(phenoxy)ethane.

9. The process of claim 1 in which said excess of bromine chloride is from about 5% to about 50% molar excess of said bis(phenoxy)alkane.

10. The process of claim 1 in which said Lewis acid catalyst is a relatively strong metal halide Lewis acid, including the steps of adding water to the reaction mixture after formation of said product to destroy the catalyst, and recovering the product by distilling off said solvent and water.

11. The process of claim 1 in which said Lewis acid catalyst is a relatively weak metal halide Lewis acid, and including the step of recovering the product by distilling off said solvent.

12. The process of claim 1 in which said catalyst is present in an amount of up to about 25% by weight of the bis (phenoxy) alkane.

13. A process for polybrominating a bis(phenoxy)alkane or bis (halo-substituted phenoxy)alkane substrate that has either two or three carbon atoms in its alkane moiety, without substantial cleavage of either phenoxy-to-alkylene linkage, comprising reacting the substrate with a molar excess of about 5% to about 50% of bromine chloride over that required for substantially complete bromination and consisting of bromine and chlorine in a molecular ratio of from about 0.7:1 to about 1.3:1, respectively, in the presence of from about 15% to about 20% by weight based on the substrate of a metal halide Lewis acid catalyst and in the presence of a chemically inert chlorinated organic solvent adapted to dissolve all of said reactants and the catalyst, under substantially anhydrous conditions, said reaction being carried out at a temperature within the range of about minus 10° C. to about 150° C. and at a pressure from about atmospheric to about 200 psig., to provide a yield of at least 77% of a product having the formula:

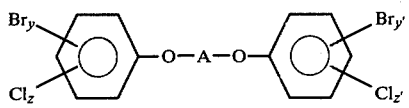

in which A is —CH₂CH₂— or —CH₂CH₂CH₂—; y and y' are independently 3, 4 or 5; and z and z' are independently 0, 1 or 2, which product is essentially fully substituted on each ring.

14. The process of claim 13 in which said product is bis(pentabromophenoxy)ethane.

15. The process of claim 13 in which said Lewis acid catalyst is selected from the bromides and chlorides of aluminum, antimony, and mixtures thereof.

16. The process of claim 15 in which said chemically inert organic solvent is a chlorinated aliphatic hydrocarbon having carbon to carbon saturation.

17. The process of claim 16 in which said catalyst is present in an amount of up to about 25% by weight of the bis (phenoxy) alkane.

18. A process for polybrominating a bis (phenoxy) alkane substrate, to substitute at least three bromines on each of the aromatic rings of said bis(phenoxy) alkane, said substrate having the formula:

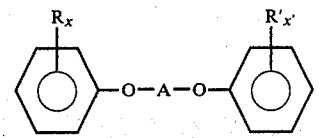

where A is —CH₂—CH₂— or —CH₂—CH₂—CH₂—; R and R' are each, independently of the other, chlorine, bromine, or alkyl up to and including four carbon atoms; x and x' are each, independently of the other, numbers from zero up to 2, without substantial cleavage in the substrate of either phenoxy-to-alkylene bridge, comprising reacting at a temperature of about minus 10° C. to about 150° C. the bis (phenoxy) alkane substrate with an amount of bromine chloride that is in stoichiometric excess of that required for the desired bromination, in the presence of an amount of a metal halide Lewis acid catalyst of at least 5% by weight based on the bis(phenoxy) alkane, under substantially anhydrous conditions, in a chemically inert organic solvent that dissolves all of said reactants and the catalyst, to form a polybrominated reaction product.

19. A process in accordance with claim 18 wherein the catalyst is selected from the bromides and chlorides of aluminum, iron, antimony, and mixtures thereof, and the solvent is a chlorinated aliphatic hydrocarbon having carbon to carbon saturation.

20. A process in accordance with claim 19 wherein the catalyst is present in an amount up to about 25% by weight of the bis (phenoxy) alkane.

21. A process in accordance with claim 20 wherein the reaction product is fully substituted and contains up to about 1.6% chlorine by weight.

22. A process for producing an essentially decabrominated bisphenoxy alkane comprising reacting at a temperature of about minus 10° C. to about 150° C. a bisphenoxyalkane having two or three carbons in the alkane moiety under anhydrous conditions with a stoichiometric excess of bromine chloride for decabromination, in the presence of a catalytic amount of a Lewis acid catalyst of at least 5% by weight based on the bis(phenoxy) alkane, and a chemically inert solvent adapted to dissolve the catalyst and reactants, to form a product having the general formula:

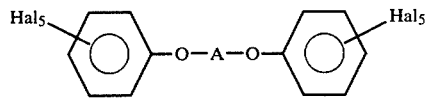

where A is alkylene of two or three carbon atoms, and Hal represents bromine, essentially without cleavage of the phenoxy-to-alkylene linkage.

23. A process in accordance with claim 22 in which the Lewis acid catalyst is selected from the bromides and chlorides of aluminum, antimony, and mixtures thereof.

24. A process in accordance with claim 23 in which the reaction is carried out at a temperature within the range from about minus 10° C. to about 150° C. and at atmospheric pressure.

25. A process in accordance with claim 24 wherein the excess of bromine chloride is from about 5% to about 50% molar excess based on the bisphenoxyalkane.

26. A process in accordance with claim 22 wherein Hal is primarily bromine but can be chlorine up to about 1.6% by weight of the product.

27. A process for producing an essentially fully brominated reaction product to be used as a fire retardant in plastic compositions comprising reacting at a temperature of about minus 10° C. to about 150° C. diphenoxyethane with an amount of bromine chloride that is in stoichiometric excess of that required for substantially complete bromination, in the presence of an amount of a metal halide Lewis acid catalyst of at least 5% by weight based on the bis(phenoxy) alkane, under substantially anhydrous conditions, in a chemically inert chlorinated solvent that dissolves the catalyst and the reactants, to form a polybrominated reaction product that is essentially fully substituted on each ring, without substantial cleavage of either phenoxy-to-alkylene bond.

28. A process in accordance with claim 27 wherein the solvent is tetrachloroethane.

29. A process in accordance with claim 28 wherein the amount of catalyst is up to about 25% by weight based on the diphenoxyethane.

30. A process in accordance with claim 29 wherein the catalyst is an antimony chloride and the amount of catalyst employed is in the range from about 15% to about 20% by weight of the diphenoxyethane.

31. A process in accordance with claim 27 wherein the reaction product contains at least 77% by weight bromine and up to 2% by weight chlorine.

32. A process in accordance with claim 30 wherein the reaction product contains at least 77% by weight bromine and up to about 1.6% by weight chlorine.

33. A process for producing an essentially fully halogenated reaction product to be used as a fire retardant in plastic compositions comprising:
(a) reacting diphenoxyethane with an amount of bromine chloride that is from about a 5% molar excess to about a 50% molar excess of that amount required for substantially complete bromination, in the presence of an antimony chloride catalyst in an amount in the range from about 15% to about 20% by weight of the diphenoxyethane, under substantially anhydrous conditions, in a tetrachloroethane solution in which the catalyst and the reactants are dissolved, at a temperature in the range from about minus 10° C. to about 150° C., at atmospheric pressure, wherein the bromine chloride consists of bromine and chlorine in a molecular ratio of from about 0.9:1 to about 1.1:1, to form a polybrominated reaction product that is essentially fully substituted on each ring;
(b) removing solvent and unreacted bromine chloride from the reaction mixture containing the polybrominated reaction product; and
(c) recovering the polybrominated reaction product as a dried product.

34. A process in accordance with claim 33 wherein the dried reaction product contains at least 77% bromine by weight and up to about 1.6% chlorine by weight.

* * * * *